(12) United States Patent
Weber

(10) Patent No.: US 6,520,773 B1
(45) Date of Patent: Feb. 18, 2003

(54) ENDODONTIC FILE

(76) Inventor: Joseph C. Weber, 6039 Ashway Ct., Indianapolis, IN (US) 46244

( * ) Notice: Subject to any disclaimer, the term of this patent is extended or adjusted under 35 U.S.C. 154(b) by 0 days.

(21) Appl. No.: 09/949,964

(22) Filed: Sep. 10, 2001

(51) Int. Cl.$^7$ .............................. A61C 3/00; A61B 5/05
(52) U.S. Cl. ........................... 433/27; 433/72; 600/589
(58) Field of Search ............................ 433/102, 32, 72; 600/589

(56) References Cited

U.S. PATENT DOCUMENTS

| | | | | |
|---|---|---|---|---|
| 3,660,901 A | * | 5/1972 | Inoue | 433/75 |
| 3,753,434 A | * | 8/1973 | Pike et al. | 433/72 |
| 3,916,529 A | * | 11/1975 | Mousseau | 433/72 |
| 5,211,556 A | * | 5/1993 | Kobayashi et al. | 433/72 |
| 6,337,994 B1 | * | 1/2002 | Stoianovici et al. | 433/72 |

OTHER PUBLICATIONS

Web Page—*www.analytic-endodontics.com/EndoAnalyzer/intro.html*.

* cited by examiner

*Primary Examiner*—Cary E. O'Connor
(74) *Attorney, Agent, or Firm*—Woodard, Emhardt, Naughton Moriarty & McNett

(57) ABSTRACT

An endodontic file having an electrically conductive stem with a bottom-cutting portion and a top head for electrically connecting to an instrument to measure the internal cavity of the tooth. A handle is mounted to the head. The middle stem portion of the stem has a surrounding insulating medium.

13 Claims, 3 Drawing Sheets

ENDODONTIC FILE

BACKGROUND OF THE INVENTION

The present invention relates generally to the field of dental tools utilized in root canal treatment.

DESCRIPTION OF THE PRIOR ART

Endodontic therapy, also known as root canal treatment, relates to treatment of the area inside of a tooth. The pulp chamber of a tooth is a hollow cavity with root canals leading from the pulp chamber to the tip of the tooth roots. The chamber and canals include pulp or nerve tissue that can be infected by bacteria leading to a tooth abscess. Root canal treatment removes all tissue within the pulp chamber and root canals which are then filled with an inert material. The calcified portion of the tooth remains alleviating the necessity for removal of the tooth.

The method of performing root canal treatment includes the step of using a dental tool to provide a passage leading to the interior or pulp chamber of the tooth. Next, an endodontic file is used to clean out the bacteria and tissue within the pulp chamber and root canal. The prior art endodontic or root canal files 10 (FIG. 1) includes an electrically conductive metal stem 11 having a non-conductive handle 12 mounted there atop. Stem 11 includes a cutting portion 13 with a plurality of cutting flutes formed thereon. The cutting portion 13 is formed on the bottom portion of the stem whereas the portion 14 located between the top of the cutting portion 13 and the bottom of handle 12 is cylindrical and smooth and does not include the cutting flutes. File 10 is manually inserted into the tooth hole leading to the interior of the tooth and is rotated and moved in and out of the hollow interior by means of the dentist twirling, pulling, and pushing handle 12 relative to the tooth. The flutes on cutting portion 13 attach to the tissue within the tooth and pull the tissue therefrom.

A manually operable file holder 15 is removably attached to stem portion 14. Holder 15, in turn, is connected to a commercially available instrument 50 by cable 51 for measuring various parameters of the interior of the tooth including the location of the tip of the canal root and canal length. For example, such an instrument includes the Endo Analyzer 8005, the Apex Finder 7005 or the Vitality Scanner 2005 available from Analytic Endodontic Products, 1717 West Collins, Orange, Calif. 92867. Likewise, the root canal file shown in FIG. 1 is also commercially available from the same organization.

File holder 15 includes a manually operable gripping end 17 releasably engageable with the non-cutting portion 14 of the file and electrically connects the file to the aforementioned instrument. The prior art files also include a passage 16 extending through the top of handle 12 allowing insertion of a string therethrough to tie the file to a stationary object alleviating the possibility of the file becoming lost or accidentally swallowed during the root canal treatment. A non-conductive washer 18 is slidably mounted to stem 11 and is moved to a position contacting the top surface of the tooth once the file is inserted to the appropriate position in the tooth thereby marking the same position for subsequent removal and reinsertion.

SUMMARY OF THE INVENTION

One embodiment of the present invention is an endodontic file comprising an electrical conductive stem having a distal end for tooth canal insertion. An electrical non-conductive handle is mounted to the stem which has an electrical conductive head on the proximal end of the stem. The handle is located between the head and the distal end.

Another embodiment of the present invention is a method of inserting an endodontic file in a tooth with the file connected to an instrument for measuring the pulp chamber and root canal of the tooth. The method includes the step of providing an endodontic file having a distal end portion, an insulating portion, and a proximal end portion electrically connected to the distal end portion but located outwardly of the insulating portion. The distal end portion is inserted into the pulp chamber and root canal of the tooth. The insulating portion is located adjacent the tooth. The proximal end portion is electrically connected to an instrument for measuring a parameter of the tooth.

It is an object of the present invention to provide an improved endodontic file.

It is a further object of the present invention to provide a new and improved method of inserting an endodontic file in a tooth and connecting the file to an instrument for measuring the pulp chamber and root canal of the tooth.

Yet a further object of the present invention is to provide an endodontic file having a top end electrically connectable to an instrument for measuring parameters of the tooth chamber.

Related objects and advantages of the present invention will be apparent from the following description.

DESCRIPTION OF THE PREFERRED EMBODIMENTS

Figure 1:
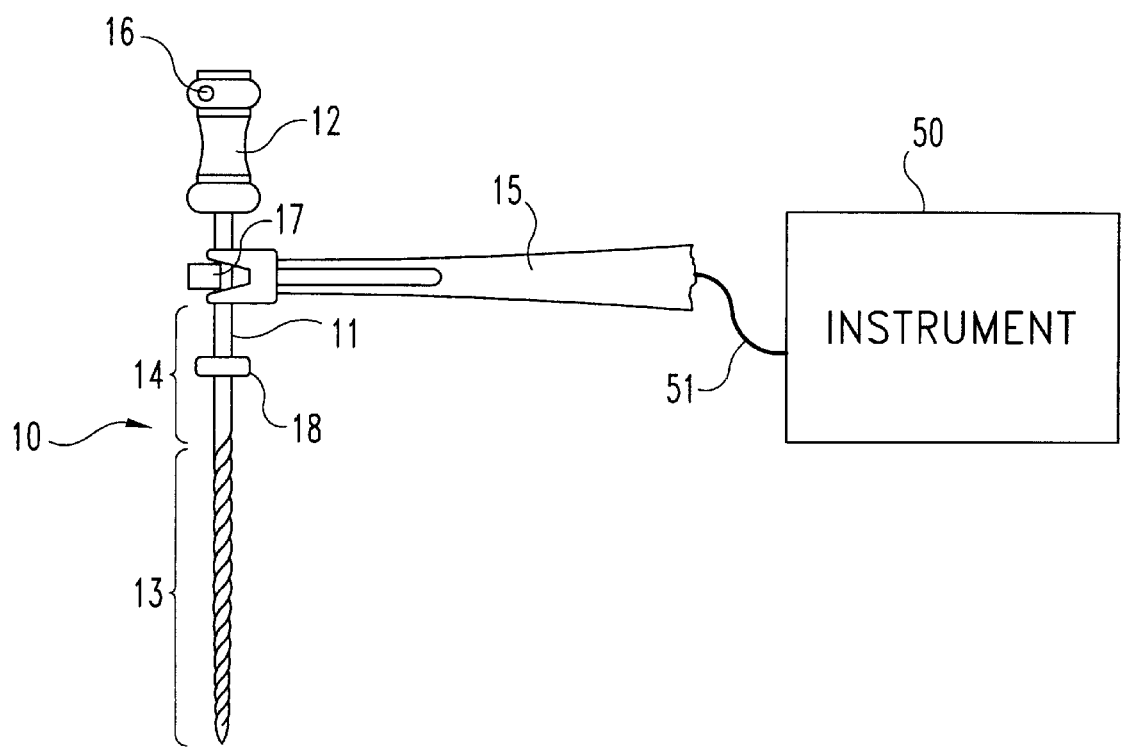
FIG. 1 is a side view of a prior art root canal file attached to a portion of a file holder.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
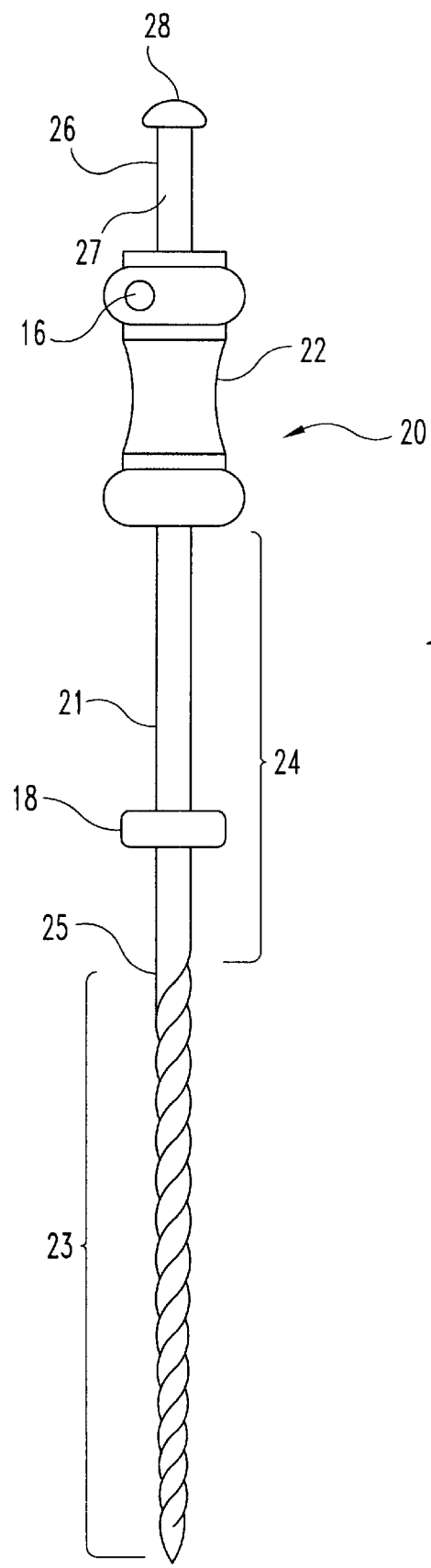
FIG. 2 is a side view of my endodontic file incorporating the present invention.
Figure 3:
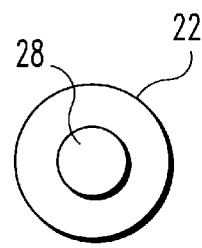
FIG. 3 is a top view of the file of FIG. 2.

Referring now more particularly to FIG. 2, there is shown my endodontic file 20 having an electrically conductive metal stem 21 with a non-conductive handle 22 mounted thereto. Stem 21 includes a bottom-cutting portion 23 with cutting flutes formed thereon and a cylindrical and smooth middle portion 24 located between the bottom of handle 22 and the top of cutting portion 23. Middle portion 24 does not include a cutting surface or the flutes present in the bottom portion 23. The cutting flutes provided on portion 23 are well known and typically include flutes having a spiral configuration extending from the bottom tip of the stem to the top 25 of the cutting portion 23. Portion 23 and 24 are integrally connected together being made from metal and thus are electrically conductive; however, portion 24 includes an outer layer of non-conductive material provided on the outer surface thereof and extending completely around the circumference of the middle portion 24 from location 25 to the bottom of handle 22. The insulating layer may include any type of insulator including plastic.

Stem 21 extends through handle 22 and is connected to a head 26 extending above handle 22. Head 26 includes a head stem 27 attached to a ball shaped top end 28. Head 26 is also made from an electrically conductive material, such as metal, and may be integrally attached to stem 21 or attached by suitable conventional means although it is mandatory that an electrical connection exist between head 26 and stem 21.

Figure 4:
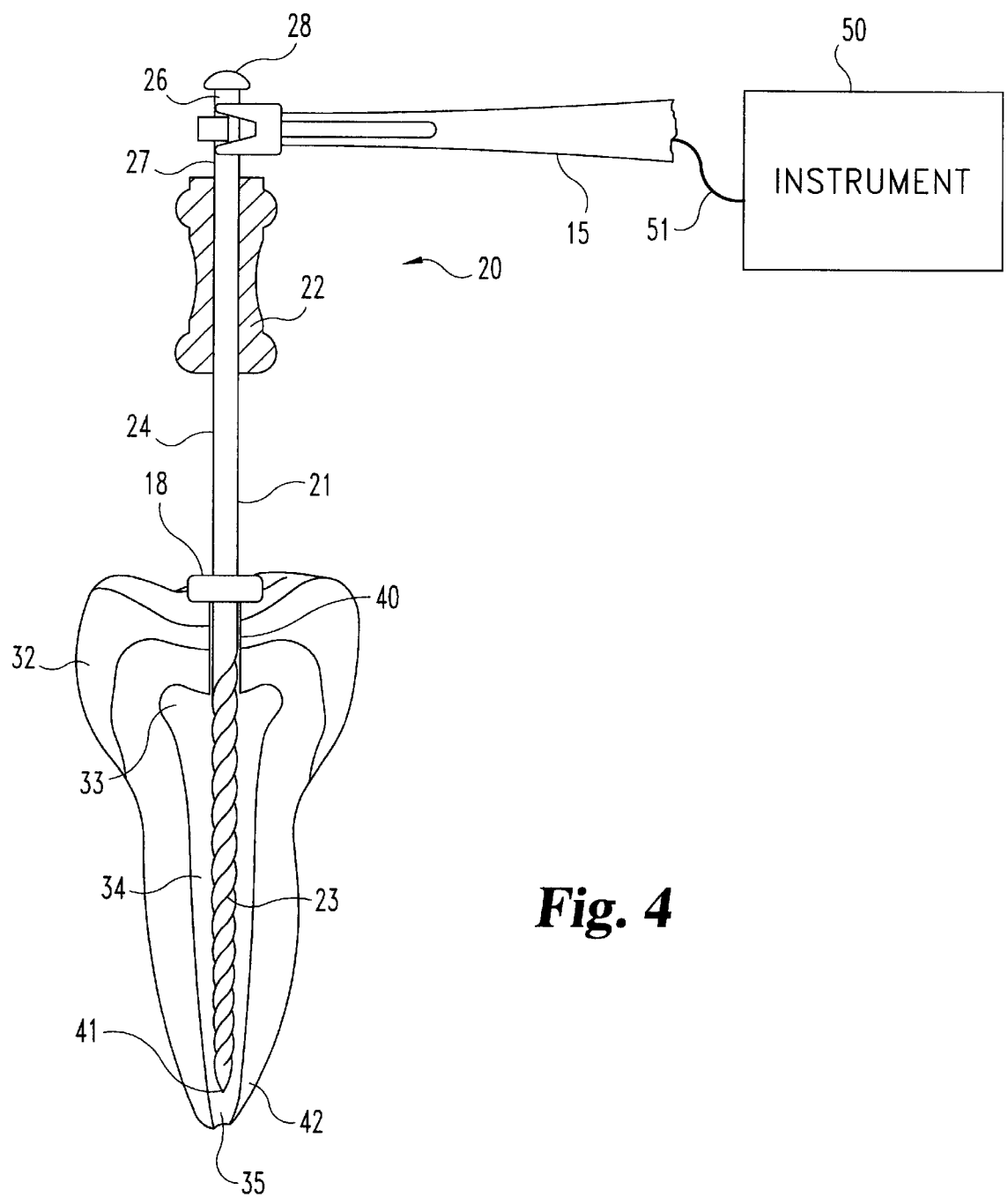
FIG. 4 is a cross-sectional view of the file of FIG. 2 inserted into a tooth and attached to the instrument file holder.

Once the entry passage 40 is drilled in tooth 32 (FIG. 4), stem 21 of file 20 is inserted through the passage and into the pulp chamber 33 and root canal 34. File holder 15 is removably attached and electrically connected to stem 27 of head 26. The commercially available aforementioned instrument 50 for measuring the interior of tooth 32 is electrically connected to via cable 51 and handle 15 to stem 21. Instrument 50 is operable to measure the length of root canal 34; however, if the tip 41 of stem 21 protrudes from the bottom 42 of tooth 32, then the stem will make electrical ground to that portion of the flesh and bone surrounding the bottom 42 of the tooth. In such a case, instrument 50 is grounded and therefore will not measure the length of the root canal. Thus, once instrument 50 indicates the tip 41 of the stem is protruding from the bottom of the root canal, the stem 21 is retracted slightly, approximately 0.5 mm, thereby positioning tip 41 at location 35 completely within the root canal 34 as depicted in FIG. 4. The electrically non-conductive washer 18 is moved downwardly along middle portion 24 until the washer abuts the outer surface of tooth 32. The washer will therefore locate the tip 41 of the stem in the appropriate location 35 once the stem is removed and reinserted until washer 18 once again contacts the outer surface of the tooth. Repeated removal and insertion of the file is necessary in order to remove the bacteria and pulp tissue within the tooth by the means of the cutting flutes on the stem.

In certain instances, the prior art files having the holder 15 attached to portion 14 (FIG. 1) will electrically ground in the location of the middle portion 14 contacting metal tooth fillings, liquid or other foreign objects. In applicant's file 20, middle portion 24 is encased in a non-conductive and insulating material with the file holder mounted to head 26 instead of middle portion 24 thereby preventing such grounding conditions.

As is the case of file 10, the new improved file 20 includes a passage 16 (FIG. 2) extending through the handle at a location so as to not intersect stem 21 thereby allowing passage of a string, for example, dental floss, through the hole to tie the file to another object preventing the file from being lost or swallowed.

The commercially available instrument handles 15 have a movable and closable gripper 17 (FIG. 1) to releasably engage the file stem. Instead of mounting holder 15 to portion 14 of file 10, the holder is mounted to stem 27 of handle 26 with the enlarged large ball shaped head 28 preventing the handle from slipping off of the top end of stem 27.

A particular advantage of file 20 results when the file is used in relation to a tooth, such as a molar tooth, located at the back of the mouth. In such a case, it is easier to connect handle 15 to the top of file 20 as compared to attaching to the middle portion 14 of file 10. Likewise, it is easier to disconnect file holder from the top of the file 20 to enable the dentist to rotate the file, or move the file to and from the tooth when cleaning the interior cavity and root canal. Likewise, a major advantage of use of file 20 is the elimination of the possibility of grounding middle portion 24 which has a surrounding electrically non-conductive material providing a barrier between the metal stem and surrounding saliva, tooth fillings and other foreign material.

The prior art files come in standard lengths including 21 mm, 25 mm and 31 mm. When treating a root canal in the back of the mouth, it is desirable to use the shortest length of file since the file must be moved to and from the tooth and rotated to remove the bacteria and pulp within the interior of the tooth. Experience has shown that at least 5 mm of stem is required to connect file holder 15 to the file. Assuming a standard root canal length of 18 mm, the length of the prior art stem must be at least 18 mm plus 5 mm or 23 mm from the tip of the stem to the bottom of handle 12. By utilizing applicant's file, holder 15 may be mounted to the handle 26 thereby allowing for a shorter stem from tip 41 to the bottom of handle 22.

Best results have been obtained by providing a file 20 having a combined length of middle portion 24 and bottom portion 23 of at least 18 mm extending from the bottom of handle 22 to the bottom tip of the stem. In the same embodiment, handle stem 27 has a length of at least 4 mm extending outwardly from handle 22.

The method of inserting the endodontic file in a tooth and connecting to an instrument by means of holder 15 for measuring the pulp chamber and root canal of the tooth includes the step of first providing the file having a distal end or cutting portion 23 and a proximal end or head 26 between which is located the insulating portion 24. The head 26 is located outwardly of the insulating portion 24 but is electrically connected to the distal end portion 23. Portion 23 is inserted into the pulp chamber and root canal of the tooth once an entry passage is drilled in the tooth. The file is inserted sufficiently into the tooth to locate the insulating portion 24 adjacent the exterior surface of the tooth. The instrument is then electrically connected by means of holder 15 to head 26 which, in turn, is electrically connected to distal end portion 23. Notably, instrument handle 15 is connected to handle 26 outwardly of both portions 23 and 24. The file is rotated while the cutting portion 23 is located within the tooth with holder 15 being held steady as the file is rotated within the grip of the handle. Alternatively, holder 15 may be disconnected from head 26 allowing the file to be moved while inserted in the tooth to facilitate removal of material within the tooth cavity and tooth canal. Once the cleaning of the interior cavity is completed, the file holder 15 may be re-connected to handle 26.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An endodontic file comprising:
  an electrical conductive stem having a distal end for tooth canal insertion and a proximal end;
  an electrical non-conductive handle mounted to said stem; and,
  an electrical conductive head provided on said proximal end with said handle located between said head and said distal end; and, wherein:

said head includes an enlarged portion and an instrument connectable portion located between said enlarged portion and said handle.

2. The file of claim 1 wherein:

said enlarged portion is ball-shaped.

3. The file of claim 1 and further comprising:

an electrical non-conductive marker slidably mounted to said stem between said handle and said distal end and movable thereon to mark canal length.

4. The file of claim 3 wherein:

said stem includes a tooth cutting surface located between said distal end and said handle.

5. The file of claim 4 wherein:

said head is integrally connected to said stem which extends through said handle, said stem has electrical insulation surrounding said stem between said tooth cutting surface and said handle.

6. A file for connecting to a tool to quantify the interior of a tooth comprising:

a metal stem with a distal end with a tooth-cutting surface extending therefrom;

a handle mounted to said stem; and, a metal head for connecting to a tool to quantify the interior of a tooth with said head connected to said stem and located outwardly of said handle.

7. The file of claim 6 wherein:

said head has an enlarged portion limiting removal of the tool therefrom.

8. The file of claim 7 wherein:

said head is integrally connected to said stem providing an electrical path therebetween, and further comprising electrical insulation surrounding said stem between said head and said cutting surface.

9. The file of claim 8 wherein:

said head has a head stem with a cylindrical cross section and a head connected to said head stem with a ball-shaped configuration.

10. The file of claim 9 wherein:

said head has a length of at least 4 millimeters.

11. A method of inserting an endodontic file in a tooth and connecting to an instrument for measuring the pulp chamber and root canal of the tooth comprising the steps of:

providing an endodontic file having a distal end portion, an insulating portion and a proximal end portion electrically connected to said distal end portion but located outwardly of said insulating portion;

inserting said distal end portion into the pulp chamber and root canal of a tooth;

locating said insulating portion adjacent the tooth; and, electrically connecting the proximal end portion to an instrument for measuring a parameter of the tooth while said insulating portion is located between said distal end portion and said proximal end portion.

12. The method of claim 11 and further comprising the steps of:

connecting said instrument outwardly of said distal end portion and said insulating portion but on said proximal end portion.

13. The method of claim 12 and further comprising the steps of:

disconnecting said connector from said distal end portion;

moving said file while inserted in said tooth; and, reconnecting said connector to said distal end portion once said moving step is completed.

* * * * *